United States Patent [19]

Guerin et al.

[11] Patent Number: 4,594,078
[45] Date of Patent: Jun. 10, 1986

[54] CONTINUOUS DIGESTER OF THE PRODUCTION OF BIOMETHANE FOR ORGANIC SUBSTANCES

[76] Inventors: Maurice Guerin, 53 Rue Victor Hugo, 71000 Macon; Patricia Ribaud, 20, Rue Emile Dubois, 75014 Paris, both of France

[21] Appl. No.: 638,459
[22] PCT Filed: Dec. 7, 1983
[86] PCT No.: PCT/FR83/00244
§ 371 Date: Jul. 27, 1984
§ 102(e) Date: Jul. 27, 1984
[87] PCT Pub. No.: WO84/02349
PCT Pub. Date: Jun. 21, 1984

[30] Foreign Application Priority Data

Dec. 8, 1982 [FR] France .................. 82 20809

[51] Int. Cl.$^4$ .............................................. C12M 1/02
[52] U.S. Cl. ...................... 48/111; 210/179; 210/180; 210/189; 435/316
[58] Field of Search ........... 48/111, 197 A; 435/167, 435/287, 316; 210/179, 180, 189, 603, 613, 256, 218, 195.1; 422/225

[56] References Cited

U.S. PATENT DOCUMENTS

| | | | |
|---|---|---|---|
| 2,050,915 | 8/1936 | Beddoes et al. | 435/167 |
| 2,538,412 | 1/1951 | Cecil et al. | 210/603 |
| 4,046,551 | 9/1977 | Anderson | 48/197 A |
| 4,342,568 | 8/1982 | Taniguchi et al. | 48/111 |
| 4,356,269 | 10/1982 | Thomsen et al. | 435/316 |

FOREIGN PATENT DOCUMENTS

| | | | |
|---|---|---|---|
| 884176 | 7/1953 | Fed. Rep. of Germany . | |
| 2419322 | 10/1979 | France . | |
| 2464627 | 4/1981 | France | 435/167 |

Primary Examiner—Arnold Turk
Assistant Examiner—Joye L. Woodard
Attorney, Agent, or Firm—Beveridge, DeGrandi & Weilacher

[57] ABSTRACT

An apparatus for the production of biomethane from organic substances comprises a digester having a vat with a floor and a centrally located vertical axis. The vat is formed by a fixed foundation and vertical side walls. A central support pillar has a vertical axis coincident with the vertical axis of the vat and is movably joined to the foundation so that the pillar can rotate about the axis. The vat has an upper portion fixed to the central pillar and rotatably supported on the side walls. A cylindrical primary compartment is located inside the vat concentrically around the central pillar. A fixed vertical partition joins the floor and radially extends between the primary compartment and the side walls of the vat. A movable partition radially extends between the primary compartment and a side wall and is capable of moving about the central axis with the upper portion and central pillar. When the movable partition moves, all substances in the vat outside the primary compartment are displaced. A recirculating pump transfers all of the substances in the vat outside the primary compartment from one side of the movable partition to the opposite side as the partition moves. A feed pump transfers substances in the bottom of the primary compartment to the top of the compartment or to the portion of the vat outside the primary compartment. Biogas is collected in a tank fixed to the upper portion of the digester and is subsequently removed from the digester.

6 Claims, 6 Drawing Figures

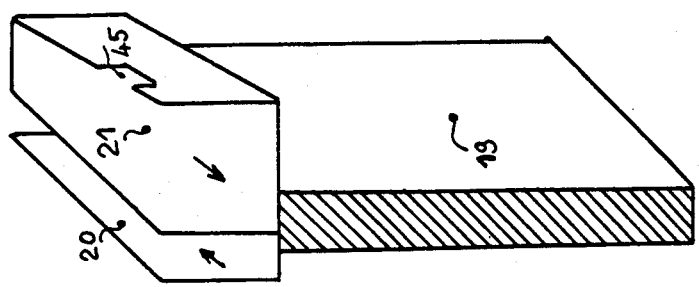
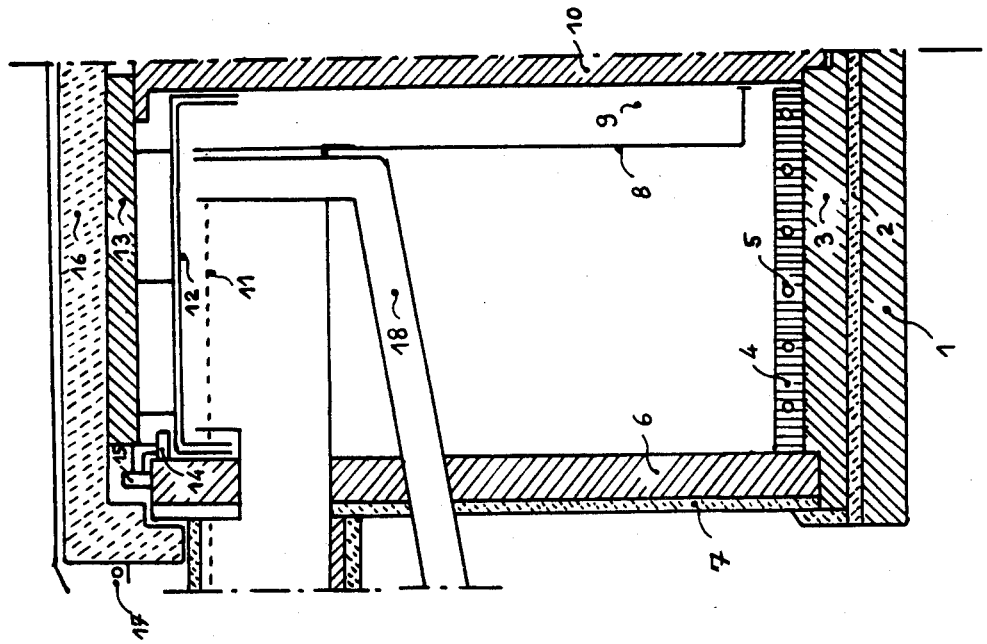

CONTINUOUS DIGESTER OF THE PRODUCTION OF BIOMETHANE FOR ORGANIC SUBSTANCES

BACKGROUND OF THE INVENTION

The present invention relates to apparatuses intended for the continuous production of biomethane from organic substances contained in animal or vegetable waste originating essentially from agriculture or industries derived therefrom.

The invention also relates to systems for the purification of effluents containing large proportions of organic matter, since fermentation which generates methane is accompanied by a substantial reduction in the BOD&5.

In the current state of the art, the internal hydraulics of continuous digesters is not well mastered. The efficacy of the mixing systems used is doubtful; moreover, they generally have disadvantages of a mechanical or biological nature. It is not known how the incoming products are divided up in the volume of products being digested.

SUMMARY OF THE INVENTION

The present invention aims to overcome the disadvantages of the prior art and proposes an apparatus for the production of biomethane from organic substances which is such that the upper part of the digester, and its central support pillar to which it is mechanically fixed, can rotate about the vertical central axis of the vat, the upper part of the digester is supported via rollers on the upper face of the side walls and on the central pillar, which is itself supported on the floor of the vat via a step bearing, the central part of the vat is occupied by a cylindrical compartment called a primary compartment, the axis of which is one with the axis of the vat of the digester, a fixed partition passes through the vat and is located along a radius of the vat, a movable partition, rigidly joined to the upper part of the digester and to the central pillar, executes circular reciprocating movements so as to sweep the whole volume of the vat outside the primary compartment, a recirculating pump and a feed pump are fixed to the upper part of the movable partition. During the displacement of the movable partition, the recirculating pump send, on either side of the partition, the whole volume swept during the displacement, and the feed pump simultaneously introduces the products originating from the bottom of the primary compartment into the stream of products being displaced under the action of the recirculating pump. The biogas is collected by a flexible tank fixed to the movable upper part of the digester.

The apparatus according to the present invention preferably comprises a movable upper part whose supporting points are such that they allow the upper part of the digester, and the elements which are joined directly or indirectly thereto, to rotate in both directions about the vertical central axis of the vat. Beams which directly or indirectly support all the movable parts are supported at one of their ends on the upper part of the central pillar and they are rigidly joined thereto. Each beam is joined at its other end to a roller with a horizontal axis, which is supported on the upper face of the side walls, and to a roller with a vertical axis, which holds them in a vertical plane. A step bearing fixed in the slab serves as a guide for the rotational movements and as a bearing for the vertical forces of the support pillar.

The apparatus according to the present invention preferably has a fixed partition. This fixed partition completely blocks the cross-section determined at the top by the bottom of the product inlet and outlet channels, at the bottom by the heated floor, towards the outside by the side wall and towards the inside by the wall of the primary compartment.

The apparatus according to the present invention preferably has a movable wall which is such that this wall is suspended from the beam which is located above it. A connecting arm joins the foot of the movable wall to the foot of the pillar by means of a rigid connection. The movable wall sweeps the whole volume located on either side of the fixed wall by moving sometimes in one direction and sometimes in the other.

The apparatus according to the present invention preferably comprises an assembly of pumps and pipes which is such that the feed pump is joined to a suction pipe originating at the bottom of the primary compartment. The feed pump directs the products originating from the bottom of the primary compartment either to the top part of the primary compartment or into the stream of products displaced by the recirculating pump. When the movable wall moves in the clockwise direction, the products are taken by the recirculating pump in front of the wall and at the foot of the wall and are thrown out behind the wall and at the top, and, symmetrically, when the wall moves in the anticlockwise direction the products are taken by this same recirculating pump and thrown out. The delivery pipe and its end are arranged in such a way that, at the end of the distance covered by the movable wall, they come above the beginning of the outlet channel after having passed through the opening.

BRIEF DESCRIPTION OF THE DRAWINGS

The present invention will be understood more clearly by studying an apparatus for the production of biomethane from organic substances, which apparatus is described by way of a non-limiting example and illustrated by the figures, in which:

FIG. 2 is a partial vertical section passing through the beginning of the outlet channel;

FIG. 3 is a bird's-eye view showing the arrangement of the end of the inlet channel and the beginning of the outlet channel, relative to the fixed partition;

DETAILED DESCRIPTION

Figure 1:
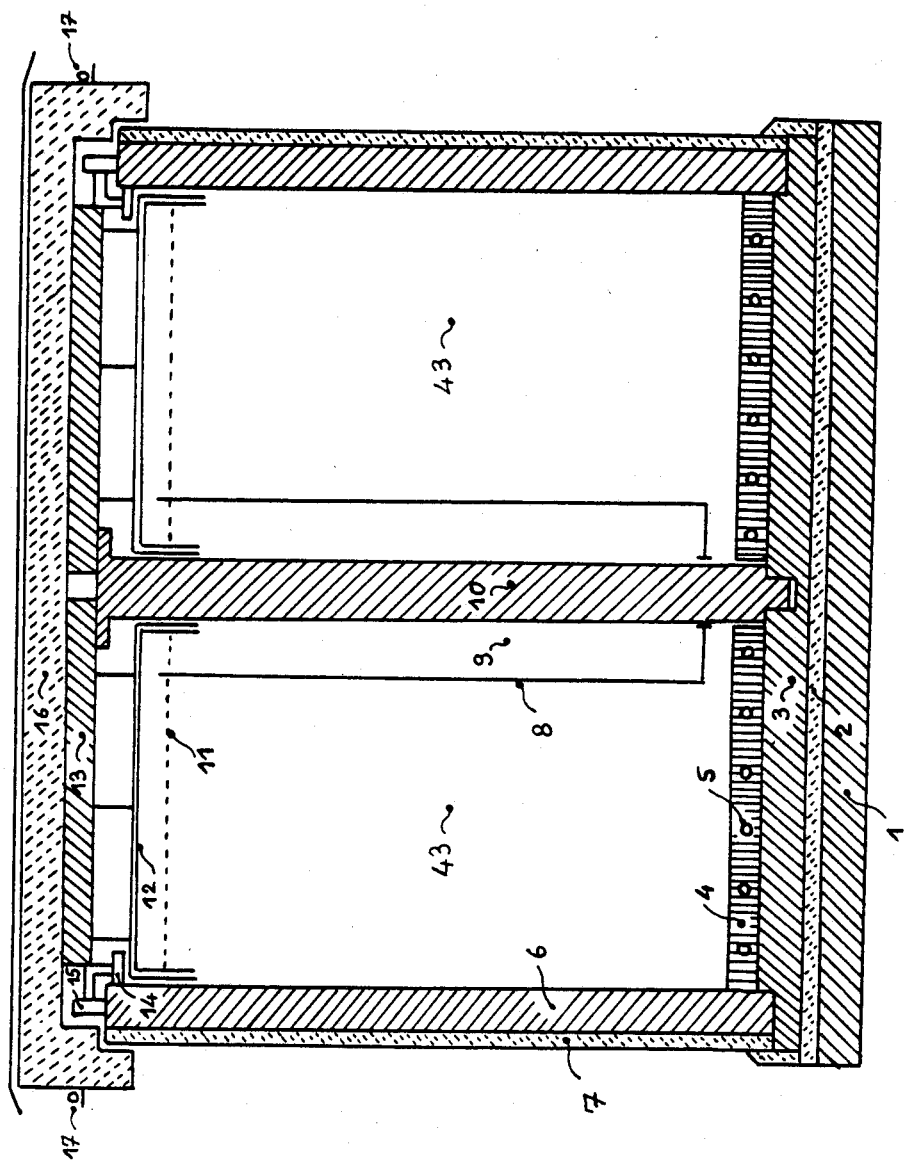
FIG. 1 is a vertical section passing through the central axis of the vat and through two rollers for suspending the upper part, which are located on either side of the central axis.

FIG. 1 shows that the base of the digester consists successively, from bottom to top, of a concrete plinth 1, a continuous layer of incompressible insulator 2, a concrete slab 3, and a heated floor 4 through which heating tubes 5 pass. Cylindrical side wall 6 is covered on the outside with a continuous layer of insulator 7.

The whole of the upper part of the digester, and its central support pillar 10 to which it is mechanically fixed, can rotate about the central axis of the vat. To allow this, a step bearing is fixed to the center of the slab 3; this step bearing accommodates the lower end of the support pillar 10 and allows it to execute alternating circular movements, serving as a guide for the rotational movements and as a bearing for the vertical forces.

At the top part, flexible tank 12 for recovering the biogas is fixed to the movable part of the digester. The side edges of the tank 12 dip into the products, the level of which is represented by the broken line 11.

The support beams 13 hold the biogas recovery tank 12, and above the support beams, there is a continuous layer of insulator 16 surmounted by a cover.

The beams 13, which directly or indirectly support all the movable parts, and in particular the whole of the upper part of the digester, are supported at one end on the upper part of the central pillar 10 to which beams 13 are rigidly joined. At the other end, each of beam 13 is joined to a roller 15 having a horizontal axis, which roller 15 supports beam 13 horizontally, and to a roller 14 having a vertical axis, which guides beam 13 vertically. The assembly comprising the central pillar 10, the roller 15 and the roller 14 allows the upper part of the digester, and the elements which are joined thereto, to rotate in both directions.

Cable 17 surrounds the external vertical side face at the level of the insulator 16. This cable is secured to a point on the side face and is connected to a reversible drive device.

The central part of the vat is occupied by primary compartment 9, the side wall 8 of which is cylindrical and has the same vertical axis as the support pillar 10 and the axis of the vat of the digester.

The remainder of the volume of the vat is occupied by secondary compartment 43.

FIG. 2 shows that biogas discharge pipe 18 starts as a vertical tube which passes from top to bottom, near the wall 8 of the primary compartment 9, through the beginning of the outlet channel 21, and then continues as an inclined tube which passes through side wall 6 and then emerges on the outside.

FIG. 3 shows fixed partition 19. This fixed partition 19, located along a radius of the vat, completely blocks the cross-section determined at the top by the bottom of the end 20 of the inlet channel and the bottom of the beginning 21 of the outlet channel, at the bottom by the heated floor 4, towards the outside by the side wall 6 and towards the inside by the wall 8 of the primary compartment 9 (the elements 4, 6, 8 and 9 are shown in FIG. 2).

The fixed partition 19 supports the end of the inlet channel and the beginning 21 of the outlet channel; the latter is fed through an opening 45 made in the side wall of the channel below the level 11 of the products in the digester (the level 11 is shown in FIG. 2).

Figure 4:
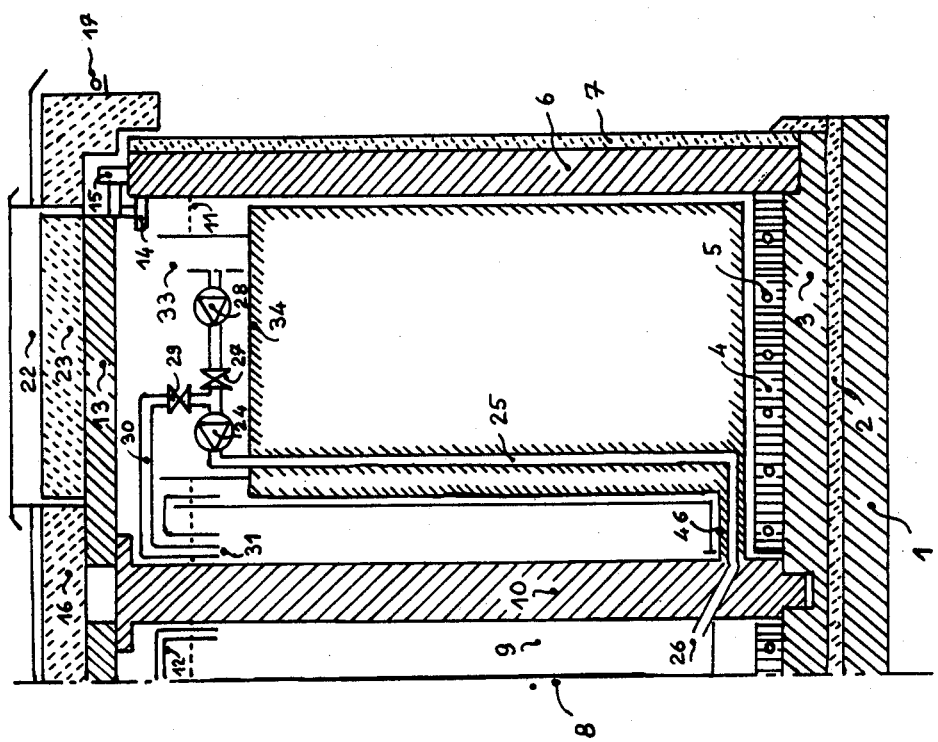
FIG. 4 is a partial vertical section passing through the central axis of the vat and through the movable wall.

FIG. 4 shows that connecting arm 46 rigidly joins the foot of the movable wall to the foot of the rotatable pillar 10. To permit this connection and the alternating rotational movement of the arm 46, the bottom of the primary compartment 9 is a sufficient distance from the heated floor 4.

At the top part of the movable wall, there is a trough 33 open at its upper part and partially immersed in the upper part of the products. The bottom 34 of this trough is horizontal and at a level such that feed pump 24 and recirculating pump 28, which are inside the trough, are under pressure.

The feed pump 24 is connected to suction pipe 25. The inlet 26 of pipe 25 is located at the bottom of the primary compartment 9.

The feed pump 24 directs the products originating from the bottom of the primary compartment 9 either to the upper part of the primary compartment, via the valve 29 and the pipe 30 which emerges at 31, or, via the valve 27, into the stream of products displaced by the recirculating pump 28.

The movable wall, which is below the trough 33, is suspended from the beam 13. The movable wall is rigidly joined to the movable upper part of the digester and the axis of rotation of the movable wall corresponds to the axis of the pillar 10.

Above the trough 33, a rectangular opening 22 (FIG. 4) passes through the cover and the whole of the layer of insulator 16. Opening 22 is blocked by a detachable insulating plug 23 surmounted by a detachable cover.

Figure 5:
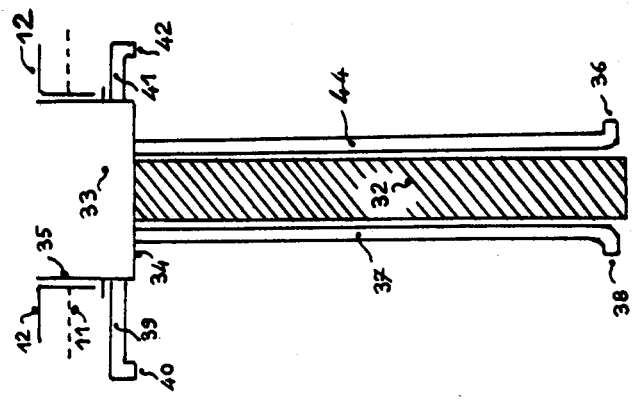
FIG. 5 is a vertical cross-section through the movable wall.

FIG. 5 shows that the movable wall 32 executes circular reciprocal movements so as to sweep the whole volume of the vat outside the primary compartment. This volume 43 (see FIG. 6) is located on either side of the fixed partition 19 (see FIG. 3).

The trough 33 is fixed by its bottom wall 34 to the upper part of the movable wall. The flexible tank 12 for recovering the biogas comes up against the side walls 35 of the trough (FIG. 5).

Suction pipe 37 is located on one side of the movable wall 32 and originates, at 38, at the foot of the movable wall. Another suction pipe 44 is on the other movable wall and its origin 36 is at the foot of the wall.

Delivery pipes 39 and 41 are located on either side of the movable wall at the upper part.

They emerge at 40 and 42, slightly below the level 11 of the products.

When the movable wall 32 moves in the clockwise direction, products are drawn through opening 38 by the recirculating pump 28 and discharged at the top at 42.

When the movable wall 32 moves in the anticlockwise direction, products are taken by this same recirculating pump 28 through opening 36 and discharged at 40.

The delivery pipe 39 and its end 40 are arranged in such a way that, at the end of the distance covered by the movable wall 32, they come above the beginning 21 (FIG. 3) of the outlet channel after having passed through the opening 45 (FIG. 3).

Figure 6:
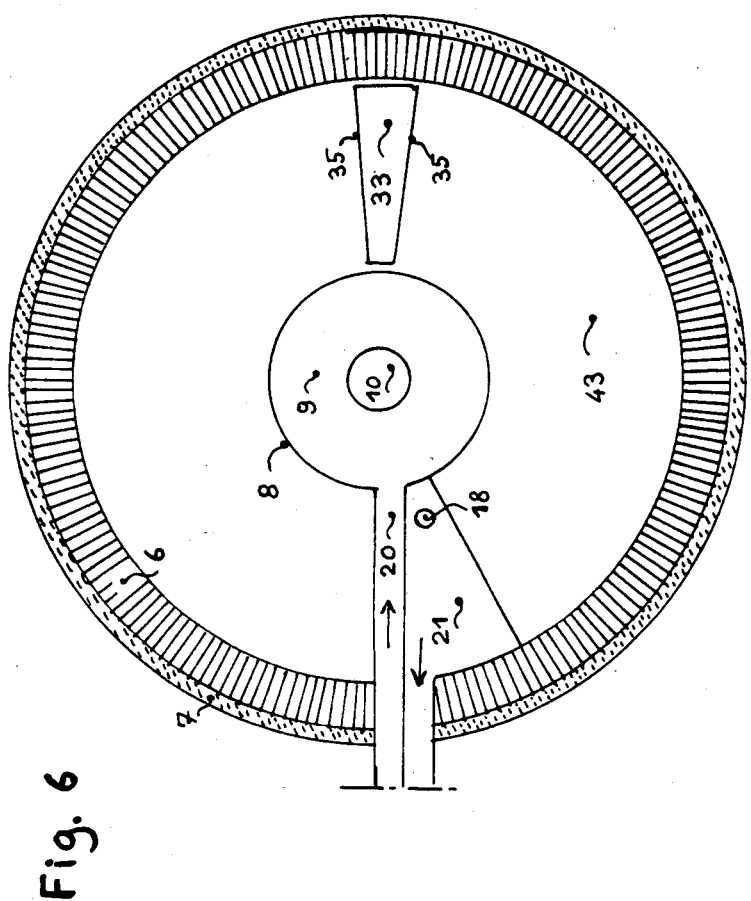
FIG. 6 is a horizontal section taken through the digester, the cutting plane passing under the side edge of the biogas recovery tank.

FIG. 6 shows that, inside the digester, the inlet channel 20 is contiguous over the whole of its path with the outlet channel 21.

The inlet channel 20 enters the digester through an opening made in the side wall 6; this opening has the same cross-section as the channel. The terminal part of the inlet channel runs into the primary compartment 9 through an opening having the same cross-section as the inlet channel.

The outlet channel 21 starts inside the digester and leaves the digester through an opening made in the side wall 6, the opening having the same cross-section as that which allows the inlet channel to pass through.

The trough 33, its side walls 35 and the movable wall located underneath have been shown in an arbitrary position.

The apparatus described above operates in the following manner.

Fresh products are introduced through the inlet channel 20. This channel is fed with waste matter by a pump, and an overflow located at the beginning of the channel keeps the level of the products constant.

The inlet channel 20 emerges at the upper part of the primary compartment 9.

The products which enter reside about 36 hours in the primary compartment 9, where they undergo depolymerization and acidification reactions.

The products are then taken from the bottom of the primary compartment by the feed pump 24, which sends them alternately to the upper part of the primary compartment 9, in order to inoculate the products which are entering, and into the stream of products being recirculated by means of the recirculating pump 28.

The movable wall 32 moves alternately in one direction and then in the other, on either side of the fixed wall 19. In the course of each displacement, it sweeps the whole of the volume of the secondary compartment 43.

During these movements, and in each direction, the recirculating pump sucks up the products in front of the movable wall, at the foot of this wall, and delivers them behind this same movable wall, and at the top of the wall, slightly below the general level of the products 11.

The output of the recirculating pump 28 is such that, over a given period of time, it is equal to the volume swept by the movable wall 32 for this same period.

When the movable wall 32 comes near the fixed wall 19 on the same side as the beginning 21 of the outlet channel, the end 40 of the pipe 39 comes above the beginning of the outlet channel 21 by virtue of the opening 45.

At this moment, the recirculating pump 28 sucks at 38, by means of the pipe 37, and delivers on the same side into the pipe 39, which makes it possible to send into the outlet channel the sludges which have accumulated in front of the movable wall 32.

The anaerobic digestion reactions which produce methane take place in the secondary compartment 43.

When the movable wall 32 approaches the beginning 21 of the outlet channel, the feed pump 24 is stopped so that there are no undigested products in the products leaving the digester.

The products leave the digester by passing through the outlet channel 21.

This channel terminates in an overflow which thus automatically keeps the products at the same constant level in the outlet channel and in the secondary compartment.

The products are heated and kept at the digestion temperature by the heated floor 4.

The biogas is collected at the surface of the products by the flexible tank 12, the side edges of which dip into the products, thus ensuring leaktightness by a hydraulic seal. The biogas leaves the digester through a pipe 18.

Traction on the cable 17 by means of a drive system, sometimes in one direction and sometimes in the other, rotates in one or other direction the whole of the upper part, the central support column 10 and the movable wall 32.

The advantages provided by the invention are the total disappearance of the problems presented by encrustation and by sedimentation of the sludges at the bottom of the digester, and also the regular and homogenous provision of nutriments throughout the bulk of the products being digested, which is a very important factor in terms of the efficiency and which permits good utilization of the buffer capacity of the products during fermentation.

What is claimed is:

1. An apparatus for the production of biomethane from organic substances, said apparatus comprising
   (A) a digester having a vat with product inlet channel means for feeding organic substances thereto and a centrally located vertical axis, wherein the vat is formed by a fixed foundation, a floor and vertical side walls secured to the foundation;
   (B) a central support pillar having a central vertical axis coincident with the vertical axis of the vat, wherein the support pillar is movably joined to the foundation so that the pillar can rotate about the axis;
   (C) an upper portion covering the vat, wherein the upper portion is fixed to the central pillar and rotatably supported on the side walls so that the pillar and the upper portion can rotate about the central vertical axis;
   (D) a cylindrical primary compartment having an open top and a bottom, said primary compartment being located inside the vat and spaced from the side walls of the vat forming a secondary compartment thereinbetween, wherein the primary compartment surrounds the central pillar and has a vertical axis that is coincident with the central vertical axis of the pillar;
   (E) a fixed vertical partition joined to the floor and radially extending across and substantially blocking a cross-section of the secondary compartment;
   (F) a movable partition having an upper part and a lower part, said movable partition radially extending across the secondary compartment, wherein said movable partition is capable of moving about the central vertical axis with the upper portion and the central pillar to displace all substances in the secondary compartment located on either side of the fixed partition by alternate movement in one direction and then in the opposite direction;
   (G) recirculating pump means and feed pump means fixed to the upper part of the movable partition;
   (H) conduit means connected to said recirculating pump for transferring from one side of the movable partition to an opposite side of the movable partition all of the substances in the secondary compartment that are displaced when the movable partition moves about the central vertical axis;
   (I) conduit means connected to said feed pump for transferring substances from the bottom of the primary compartment alternately (1) to the top of the primary compartment, and (2) to the secondary compartment; and
   (J) flexible tank means fixed to the upper portion for collecting biogas formed in the digester.

2. Apparatus according to claim 1 wherein
   the upper portion is supported by beam means that are centrally supported by and secured to the pillar and peripherally supported by the side walls, wherein peripheral support is provided by roller means having a horizontal axis of rotation and roller means having a vertical axis of rotation; and
   the foundation has step-bearing means therein for supporting the central pillar and for guiding rotational movement of the pillar.

3. Apparatus according to claim 1 comprising
   heating means located in the floor for heating substances in the vat;

the product inlet channel means located above the fixed partition and in communication with the primary compartment for feeding organic substances to the digester; and product outlet channel means located above the fixed partition and in communication with the tank means for removing biogas from the tank.

4. Apparatus according to claim 2 wherein the movable partition is suspended from the beam; and the movable wall is rigidly joined to the central pillar by a connecting arm.

5. Apparatus according to claim 1 wherein the conduit means connected to the recirculating pump includes a suction port proximate the floor of the vat on one side of the movable partition and a discharge port above the suction port and on an opposite side of the movable partition.

6. Apparatus according to claim 5 wherein the discharge port extends over the product outlet channel means when the movable partition is adjacent the fixed partition.

* * * * *